United States Patent
Kim et al.

(10) Patent No.: US 6,623,696 B1
(45) Date of Patent: Sep. 23, 2003

(54) BIOCHIP, APPARATUS FOR DETECTING BIOMATERIALS USING THE SAME, AND METHOD THEREFOR

(75) Inventors: Su-Hyeon Kim, Seoul (KR); Jo-Kyun Park, Seoul (KR); Tae-Han Kim, Seoul (KR)

(73) Assignee: LG. Electronics, Inc., Seoul (KR)

( * ) Notice: Subject to any disclaimer, the term of this patent is extended or adjusted under 35 U.S.C. 154(b) by 125 days.

(21) Appl. No.: 09/697,171

(22) Filed: Oct. 27, 2000

(30) Foreign Application Priority Data

Oct. 29, 1999 (KR) .......................... 1999/47571

(51) Int. Cl.[7] .................. G01N 21/00; G01N 31/22; C12Q 1/68; C12M 1/34; C12M 3/00
(52) U.S. Cl. .................. 422/58; 422/50; 422/64; 422/68.1; 435/287.2; 435/6; 436/164
(58) Field of Search .................. 436/164; 435/287.2, 435/6; 422/64, 50, 58, 68.1; 204/451; 365/151

(56) References Cited

U.S. PATENT DOCUMENTS

| | | | |
|---|---|---|---|
| 5,091,652 A | 2/1992 | Mathies et al. .......... 250/458.1 |
| 5,143,854 A | 9/1992 | Pirrung et al. .......... 436/518 |
| 5,474,796 A | 12/1995 | Brennan .......... 427/2.13 |
| 5,755,942 A * | 5/1998 | Zanzucchi et al. .......... 204/454 |
| 6,067,246 A * | 5/2000 | Heller et al. .......... 365/151 |
| 6,207,031 B1 * | 3/2001 | Adourian et al. .......... 204/451 |
| 6,212,158 B1 * | 4/2001 | Ha et al. .......... 369/275.4 |
| 6,338,620 B1 * | 1/2002 | Yamada et al. .......... 422/64 |
| 6,342,359 B1 * | 1/2002 | Lee et al. .......... 435/6 |
| 6,391,625 B1 * | 5/2002 | Park et al. .......... 435/287.2 |

* cited by examiner

*Primary Examiner*—Jill Warden
*Assistant Examiner*—Brian Sines
(74) *Attorney, Agent, or Firm*—Morgan, Lewis & Bockius LLP

(57) ABSTRACT

The present invention provides a biochip which includes: a substrate having a center hole at a central portion, an biomaterial region aranged at a circumferential portion of the top surface of the substrate; and an information region formed on the substrate between the biomaterial region and the center hole and having the information on the biomaterials. In the method for detecting biomaterials using the biochip, a disk-type upper substrate is placed on the top surface of the biochip, a sample is put between the disk-type upper substrate and the biochip, the reaction between the sample solution and the biomaterial of the biochip is accelerated by rotating the biochip, and the detection unit analyzes the biomaterial by receiving the light emitted from the biomaterials, thereby making it possible to analyze the biomaterial of the sample solution. Since the biochip of the present invention is constructed as a disk type, high-priced scanning equipment is not necessary for thereby reducing the cost for detecting biomaterials. Since the sample solution is stirred by rotating the biochip, the speed of binding reaction is increased for thereby decreasing the time for analysis. Since the information on the biomaterial and the analytical information of the biomaterial can be recorded in the biochip, the management of the information of the biomaterials is made easier.

14 Claims, 3 Drawing Sheets

BIOCHIP, APPARATUS FOR DETECTING BIOMATERIALS USING THE SAME, AND METHOD THEREFOR

BACKGROUND OF THE INVENTION

1. Field of the Invention

The present invention relates to a biochip, and more particularly, to a biochip capable of detecting other biomaterials by immobilizing biomaterials, such as DNA or protein, on a substrate, apparatus for detecting biomaterials using the biochip, and method therefor.

2. Description of the Background Art

Generally, the strength of a non-covalent bond, such as an ion bond, hydrogen bond, and van der waals bond, in an aqueous solution is very small, which is 1/30~1/300 times smaller than the strength of a covalent bond, thus making it difficult to have a stable bond. However, since a macromolecule has a large number of binding sites, it can maintain a stable bond at an ambient temperature. Such a non-covalent bond helps a specific molecule to selectively recognize other molecules.

The above molecule recognizing other molecules is defined as a receptor in a broad sense, which includes, for example, a membrane protein transferring a signal from a cell surface into a cell membrane, oligonucleotides or peptide nucleic acids(PNA) recognizing a predetermined sequence of DNA, antibody relating to an immune reaction, enzyme conducting hydrolysis of metabolite, and the like. And, the material selectively binding to these receptors is referred to as a ligand.

The Southern blotting, a method for detecting DNA having a specific base sequence, was developed by Edwin Southern in 1975. The DNA fragments of a test sample are separated by size by means of electrophoresis, and the separated DNA fragments are moved onto a solid substrate made of nitrocellulose or nylon membrane, thereby maintaining the relative position of the DNA fragments. Afterwards, the probe DNA or RNA having a specific base sequence which is labeled with a radioisotope is put into the DNA fragment immobilized on the solid substrate. Since the DNA or RNA put therein for use as a probe is bonded to the DNA fragments which can be complementarily bonded, by hybridization, it is possible to know the position of the DNA having a specific base sequence.

By applying this method, the Northern blotting for analyzing RNA and the Western blotting for analyzing protein were developed, and their principle is similar to that of the Southern blotting.

Such a number of methods using a binding reaction between a receptor and a ligand are employed in many fields, such as biological researches, medical diagnosis, new drug screening, forensic medicine, etc., most of which relate to a limited number of receptors and ligands.

For example, in case of making a DNA having four kinds of bases and having a sequential sequence of 10 bases, the DNA has a wide variety of structures with about more than 1,000,000 molecular types.

Therefore, an experiment for the binding reaction between a receptor and a ligand requires a very repetitive experimental procedure, and accordingly requires much labor forces, time, and enormous resources.

To solve this problem, there has been developed a biochip technique for forming a two-dimensional array of a plurality of receptors and ligands at a known position on a substrate.

Biochips are classified into DNA chip formed by using a DNA probe, protein chip formed by using an enzyme, antigen/antibody, bacteriorhodopshin, etc., and cell chip formed by using a cell, according to the type of a used biomaterials.

In this biochip method, it is important to integrate many kinds of probes on a single chip. It is reported that a DNA chip with 400,000 probes can be arranged on the substrate according to the conventional art.

The DNA chip is a high-density array of DNA fragments having a wide variety of base sequences on a narrow surface of the substrate, which is used to find out information on the DNA in an unknown sample by hybridization of an immobilized DNA and the unknown DNA sample.

Here, the hybridization means that gene subsequences are linked each other to form double-stranded DNA by complementary base pairing of hydrogen bond between the DNA bases of adenine-thymine (A-T), guanine-cytosine (G-C).

Hence, the unknown DNA sample is hybridized with DNA probes immobilized on the substrate, it is possible to learn about the base sequence of the DNA in the test sample by appropriately labeling the double-stranded DNA, or DNA probe or DNA sample.

Meanwhile, the fabrication methods for a DNA chip are mainly classified into a synthesis method for making a probe by directly synthesizing oligonucleotides on a substrate and a method for placing pre-synthesized nucleic acids (oligonucleotides, cDNA; complementary DNA, PNA; peptide nucleic acids, etc.) on a substrate.

The first method is a method using a photolithography frequently used in a semiconductor process disclosed in the U.S. Pat. No. 5,143,854. In this method, a functional group capable of synthesizing a nucleotide protected by a photolabile chemical material is introduced in advance onto a substrate. And then, a light is emitted on the predetermined positions by using photomask so that photolabile chemical material is removed and only the functional group that can be reacted with the nucleotide is exposed. Since each nucleotide participating in the reaction is also protected with a photolabile material at its end, the nucleotide can be synthesized one by one only in the position activated by exposure to light. Thereafter, non-reacted nucleotides are removed, and the process for selectively synthesizing a nucleotide on the substrate using other photomask pattern is repeated, resulting in forming oligonucleotides having a desired nucleotide sequence on the substrate.

Another method is a method for forming oligonucleotides on the surface by electrically discharging any one of four bases by piezoelectric printing as in the case of an ink jet printer. This method is disclosed in the U.S. Pat. No. 5,474,796.

Still another method is a method for arraying a pre-synthesized DNA on a substrate by mechanical microspotting, which is disclosed in Science 270 (1995), 467–470p. This method is disadvantageous in that a high density DNA fabrication is impossible and mass production is impossible, so it is mainly applied to a DNA chip fabrication for use in research fields.

As described above, the conventional methods of DNA chip fabrication are somewhat different, but have a common characteristic that different DNA molecules are arranged on a rectangular substrate of a predetermined size in a checker figure. In addition, fluorescence is measured in order to know the result of hybridization reaction. Since the DNA chip is fabricated by using a rectangular substrate, a high-priced image scanner is required to scan the surface of a two-dimensional substrate. The information on the image scanner is disclosed in the U.S. Pat. No. 5,091,652.

The above biochip and apparatus for detecting biomaterials according to the conventional art have the following disadvantages.

Firstly, high-priced equipment is required, and much time is needed in order to analyze the biological reaction patterns of the biochip.

Secondly, it takes much time for analysis because DNA molecules in the sample move to the surface by simple diffusion until they are hybridized with probes on the surface.

SUMMARY OF THE INVENTION

Accordingly, the present invention provides a biochip which is fabricated at a low cost, conducts a rapid analysis using a small amount of samples, and stores much information on biomaterials, apparatus for detecting biomaterials, and method therefor.

To achieve the above object, there is provided a biochip according to the present invention which includes:

a substrate having a center hole at a central portion; a biomaterial region arranged at a circumferential portion of the substrate; and an information region formed on the substrate between the biomaterial region and the center hole.

In addition, there is a biochip according to the present invention which has a disk-type substrate, and is made of any one of glass, silicon, acryl group, polycarbonate, PET (polyethylene terephtalate), polystyrene, and polypropylene.

In addition, there is provided a biochip according to the present invention in which the biomaterials are immobilized on the substrate, and are arranged at the same interval in a radial direction of the substrate and at the same angle in a circumferential direction of the substrate.

In addition, there is provided a biochip according to the present invention in which the information region has slits spaced so as to have a predetermined interval and has a reference slit for providing information on a reference position.

In addition, there is provided a biochip according to the present invention in which the width of the reference slit is different from that of other slit.

In addition, there is provided a biochip according to the present invention in which the slits are formed of gold or aluminum.

In addition, there is provided an apparatus for detecting biomaterials according to the present invention which includes:

a biochip having a substrate having a center hole at a central portion, a biomaterial region arranged at a circumferential portion of the substrate, and an information region formed on the substrate between the biomaterial region and the center hole; a spindle motor mounted at the center hole of the biochip and adapted to rotate the biochip; first and second light sources for irradiating light to the biochip; a mirror unit for selectively reflecting or transmitting the light emitted from the first light source according to its wavelength; a head unit for receiving the light transmitted from the mirror unit and irradiating the same to the biomaterial region of the biochip; a detection unit for detecting the light emitted from the biomaterial region and analyzing the biomaterial; and an optical pickup unit for recording the information on the biomaterials on the information region of the biochip and detecting the same by means of the light emitted from the second light source.

There is provided an apparatus for detecting biomaterials according to the present invention in which the head unit moves in a radial direction of the biochip.

There is also provided an apparatus for detecting biomaterials according to the present invention in which the mirror unit is a dichroic mirror, an apparatus for detecting biomaterials in which the detection unit is an APD(avalanche photodiode) or PMT(photo-multiplier tube).

There is also provided an apparatus for detecting biomaterials according to the present invention which further includes an optical filter, lens, and pin hole between the mirror unit and the detection unit.

In a method for detecting biomaterials using the apparatus for detecting biomaterials, including: a biochip having a substrate having a center hole at a central portion, a biomaterial region arranged at a circumferential portion of the substrate, and an information region formed on the substrate between the biomaterial region and the center hole; a spindle motor mounted at the center hole of the biochip and adapted to rotate the biochip; first and second light sources for irradiating light to the biochip, a mirror unit for selectively reflecting or transmitting the light emitted from the first light source according to its wavelength, a head unit for receiving the light transmitted from the mirror unit and irradiating the same to the biomaterial region of the biochip; a detection unit for detecting the light emitted from the biomaterial region and analyzing the biomaterial; and an optical pickup unit for recording the information for biomaterials on the information region of the biochip and detecting the same by means of the light emitted from the second light source, there is provided a method for detecting biomaterials according to the present invention which includes the steps of: mounting a biochip to the spindle motor; putting a sample solution into the biomaterial region of the biochip and rotating the biochip; emitting the light from the first light source to thus be incident upon the biomaterials of the biochip; making the light emitted from the biomaterials incident upon the detection unit and analyzing the biomaterials; and recording the information for biomaterials on the information region of the biochip and detecting the same by means of the pickup unit.

There is also provided a method for detecting biomaterials according to the present invention in which the step of rotating the biochip includes the steps of: placing the upper substrate on the biochip; putting sample solution between the upper substrate and the biochip; and helping to diffuse the sample solution by rotating the biochip.

Additional advantages, objects and features of the invention will become more apparent from the descriptions which follows.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION OF THE PREFERRED EMBODIMENTS

The structure of a biochip according to the present invention will now be described with reference to the accompanying drawings.

Figure 1:
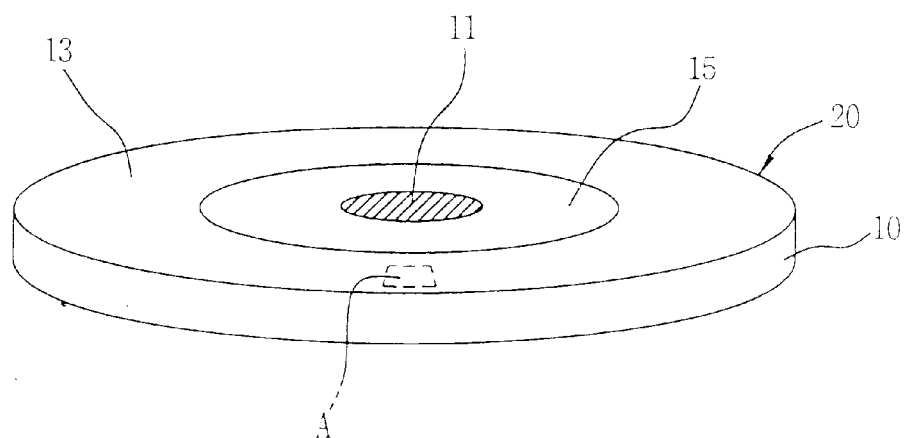
FIG. 1 is a perspective view illustrating the structure of a disk-type biochip according to the present invention.
Figure 2:
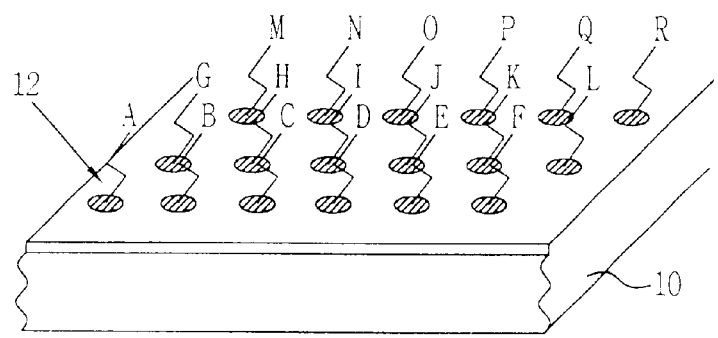
FIG. 2 is an expansion view of a block(A) in dotted line, e.g., biomaterial region.
Figure 3:
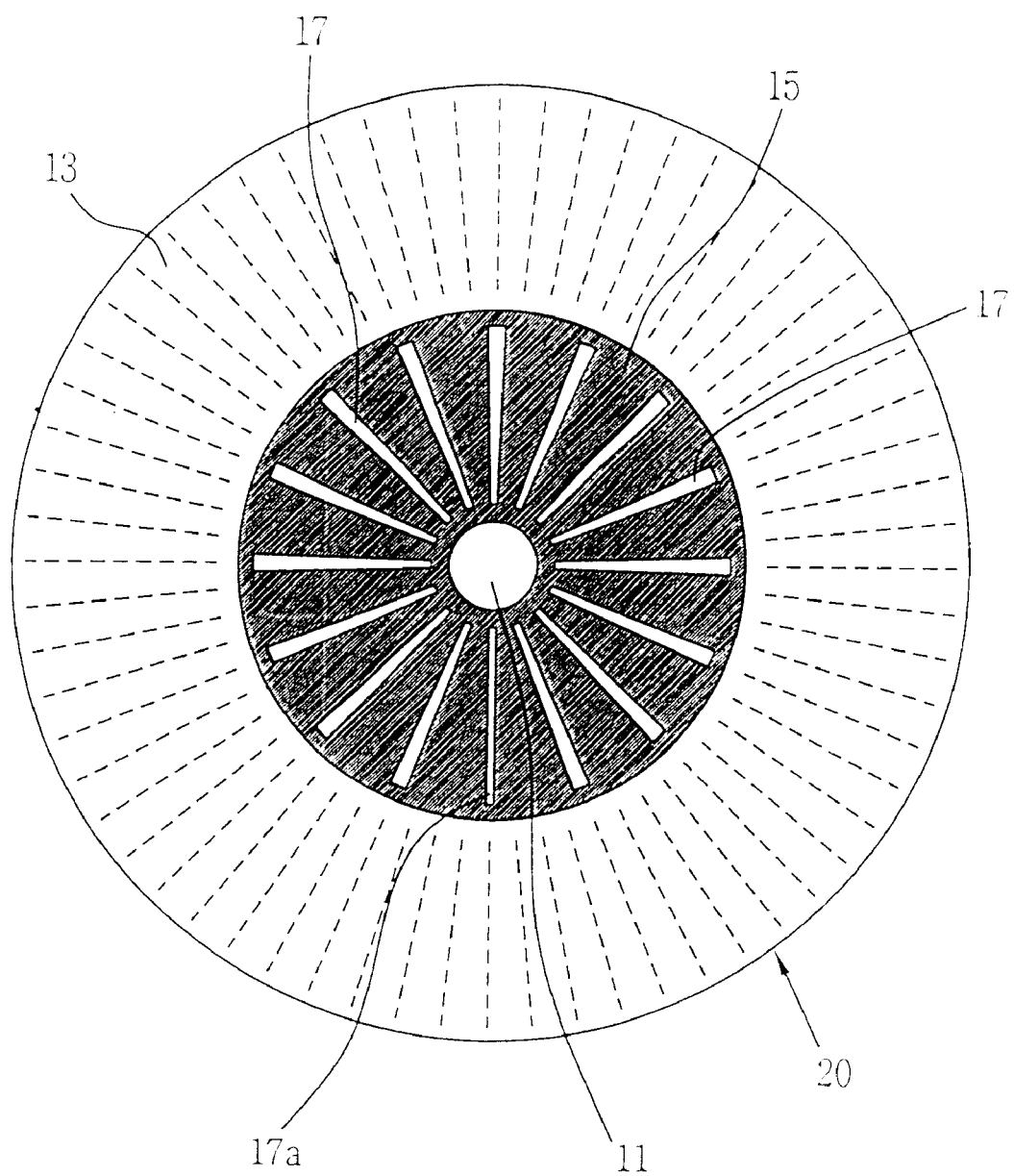
FIG. 3 is a detailed plane view of FIG. 1.

FIGS. 1, 2, and 3 are a perspective view, expansion view, and plane view, respectively, illustrating the structure of the biochip according to the present invention. That is, FIG. 2 is an expansion view of a block(A) in dotted line, e.g., biomaterial region, and FIG. 3 is a detailed plane view of FIG. 1.

As illustrated therein, the biochip 20 according to the present invention includes:

a disk-type substrate 10 having a center hole 11 formed at the center; a biomaterial region 13, which is an upper circumferential region of the disk-type substrate 10; and an information region 15 formed on the top surface of the disk-type substrate 10 between the biomaterial region 13 and the certer hole 11. The biomaterial region 13 is a region in which biomaterials 12 (refer to FIG. 2) immobilized on the top surface of the disk-type substrate 10. The information region 15 is a region on which the information of the biomaterials 12 of the biomaterial region 13 and the position information of the biomaterials 12 are recorded. In addition, the information region 15 can have a plurality of slits 17.

Meanwhile, the substrate 10 is made of an inorganic materials, such as glass and silicon, or polymer material, such as acryl group, PET, polycarbonate, polystyrene, and polypropylene.

The biomaterial 12 is one of DNA, RNA, PNA, oligonucleotides, peptides, protein, membrane, polysaccharides, antigen, antibody, and cells.

In addition, as illustrated in FIG. 2, the biomaterial 12 is immobilized on the surface of the biomaterial region 13 on the substrate by a covalent binding. Different biomaterials are immobilized in their respective position (distance from the center of the substrate, angle from the reference point of the substrate) on the substrate 10.

Here, the above-mentioned different biomaterials indicate the molecules having different base sequences or amino acid sequences, in case of DNA or peptide chips. In a predetermined region, a biomaterial having the same structure is immobilized.

And, the substrate forms slits 17 having a predetermined interval at the information region 15 of the substrate, as illustrated in FIG. 3, in order to obtain the information on positions using a laser light.

These slits 17 are fabricated by being coated with metal, such as gold(Au) or aluminum, as a reflecting layer. At this time, in order to set a reference position in the information region 15 of the disk-type substrate 10. any one of these slits 17 is set as a reference slit 17a, and this reference slit 17a has a different width from other slits.

In this way, the information on the positions in the information region 15 of the substrate 10 can be read out using an optical signal, such as reflection and transmission, or an electric and magnetic signal.

Meanwhile, in order to immobilize the biomaterial to the substrate, a polymer material having a functional group, such as —$NH_2$ or —OH, is grafted on the substrate. Continuously, the biomaterial is synthesized on the substrate by using photolithography or inkjet method, or the biomaterial already obtained by synthesis or separation is spotted, thereby bonding the biomaterial to the substrate.

At this time, the biomaterial is arranged at the same interval in a radial direction, and at the same angle in a circumferential direction as illustrated in FIG. 3.

After immobilizing the biomaterial on the substrate 10 by the above-mentioned methods a sample solution labeled with a fluorescent material is placed on the substrate and then reacted with the biomaterial immobilized on the disk-type substrate under general reaction conditions, thus making it possible to monitor the degree of a selective binding.

Here, the sample is in the state of being amplified by a method such as PCR (polymerase chain reaction) and being covalently-bonded with an appropriate fluorescent material.

Meanwhile, a probe can recognize an unlabeled molecular binding in such a manner that a fluorescent signal is changed by a selective binding with the corresponding molecule in the sample, because a fluorescent donor and a quencher are labeled to a single molecule.

In addition, the label material is an ethidium bromide for recognizing a binding reaction between the sample and a probe and making a signal by selectively binding to the bond between the sample and the probe, and is a molecule which is excited by an excitation light and emits fluorescence.

Here, the excitation light is a laser.

Figure 4:
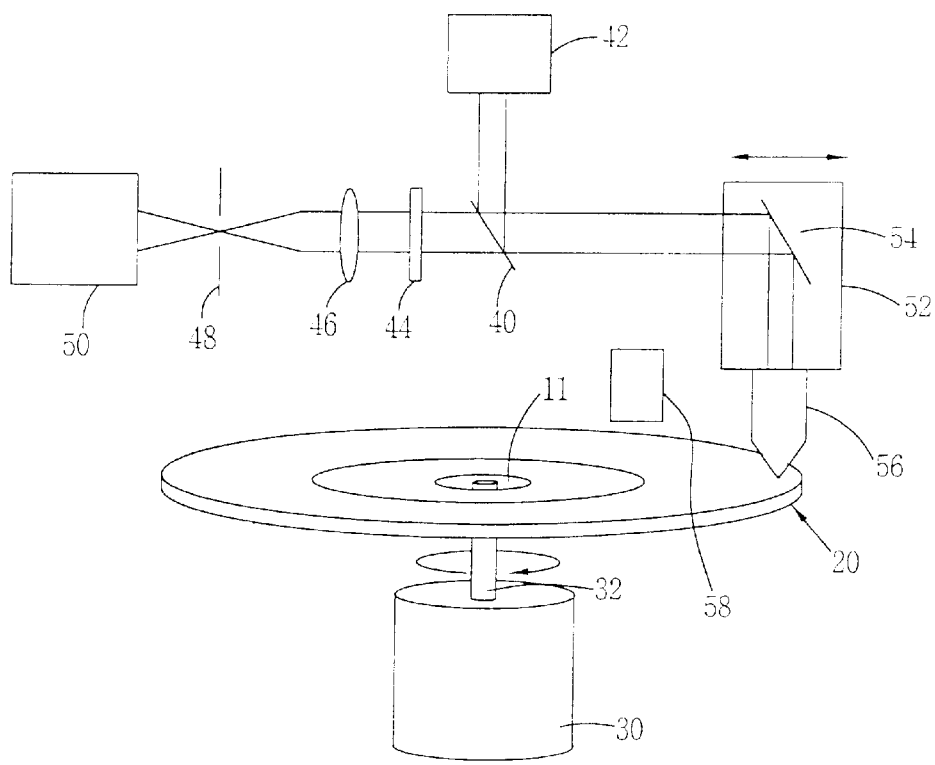
FIG. 4 is a schematic view of an apparatus for detecting biomaterials using the biochip according to the present invention.

The detection of biomaterials using the thus constructed biochip according to the present invention can be analyzed by using the apparatus for detecting biomaterials as illustrated in FIG. 4.

As an apparatus for detecting biomaterials of the biochip according to the present invention, as illustrated in FIG. 4, a confocal-type disk reader is used.

The construction of the apparatus for detecting biomaterials of the biochip will now be described. First, a spindle motor 30 for rotating the biochip 20 according to the present invention as illustrated in FIGS. 1 through 3 is installed The spindle motor 30 is connected to a rotating shaft 32, said rotating shaft 32 being inserted into the center hole 11 of the biochip 20

In addition, a dichroic mirror 40 is installed at the upper portion of the biochip 20, and a laser light source 42 is installed at the upper portion of the dichroic mirror 40.

Meanwhile, an optical filter 44 is installed at the front side of the dichroic mirror 40 in a horizontal direction, a lens 46 is installed at the front side of the optical filter 44, a pin hole 48 is installed at the front side of the lens 46, and a photomultiplier tube 50 is installed at the front side of the pin hole.

In addition, at the rear side of the dichroic mirror 40, a head unit 52 operated by being connected to a linear motor(not shown) is installed at the upper portion of the biochip 20. A mirror 54 is installed at the top portion of the head unit 52, and an objective lens 56 is installed at the lower side thereof.

In addition, an optical pickup device 58 is installed at the upper side of the biochip 20.

The method for detecting biomaterials using the apparatus for detecting biomaterials having the structure of FIG. 4 will be described.

Figure 5:
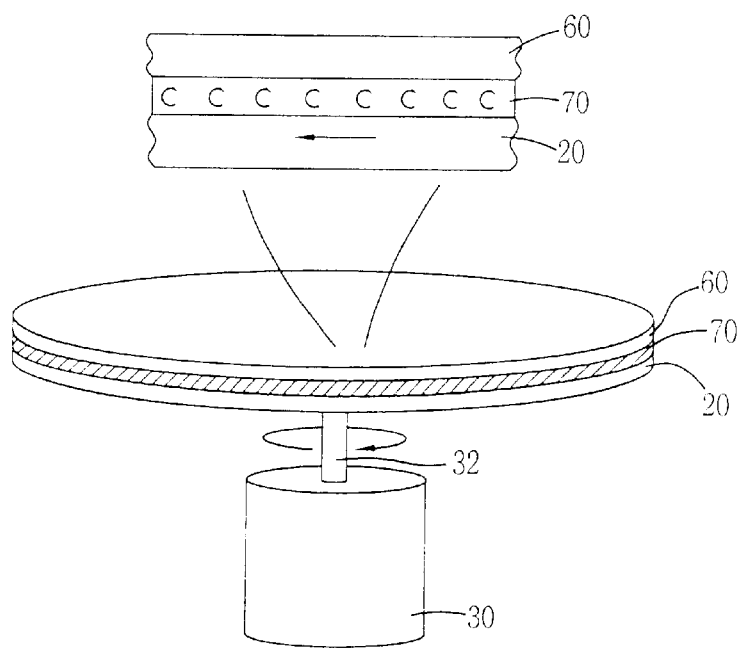
FIG. 5 illustrates the figure of an apparatus for stirring solution before detecting biomaterials.

First, the biochip 20 is mounted on the spindle motor 30, and is rotated by operating the spindle motor 30. At this time, as illustrated in FIG. 5, the disk-type upper substrate 60 is mounted on the top surface of the biochip 20, and the biochip 20 rotated in the state that a sample solution 70 is put between the disk-type upper substrate 60 and the biochip 20.

The speed of binding reaction between biomaterials exert an important effect upon the time for analysis. In particular, it takes much time for the biomaterials in a probe sample immobilized on the surface of the substrate to be diffused and reacted with one another. Therefore, the diffusion of the sample is rapidly performed by obtaining the effect of stirring the sample solution by rotating the biochip 20, this increasing the reaction speed.

Here, the upper substrate 60 place on the biochip 20 is preferably made of a polymer material, such as teflon, on which biomaterial cannot be adsorbed.

Continuously, the laser light from a semiconductor laser, e.g., the laser light source 42, is incident upon the head unit 52 via the dichroic mirror 40 for selectively reflecting or transmitting light according to its wavelength.

The head unit 52 is connected to the linear motor and moves in a radial direction of the substrate, and is constructed of optical elements, such as an objective lens 56 and mirror 54. The laser light incident upon the head unit 52 is focused on the biomaterial of the substrate via the objective lens 56. The emitted fluorescence is collected with the objective lens 56 and is incident upon the dichroic mirror 40 again via the mirror 54 of the head unit 52.

Here, since the fluorecence has a longer wavelength than the laser light, it passes through the dichroic mirror 40, and is applied to a photodetection unit, such as the photomultiplier tube(PMT) or APD(avalanche photodiode) via the optical filter 44, lens 46, and pin hole 48 for signal processing and analysis.

Since the photomultiplier tube 50 or APD has a photomultiplication ability, it changes light into electric signals with high sensitiveness.

At this time, in case of using more than two kinds of fluorescent molecule, it is possible to analyze a number of samples at a time by detecting other wavelengths from the fluorescent molecule by using more than one or two lasers The information of the probe reacted with the sample can be known by measuring the rotating angle of the substrate and reading out the information on the position of a region for measuring fluorescence by using an extra optical pickup unit 58 during the rotation of the biochip 20.

In this position information region, the information of the biomaterial immobilized on the surface can be recorded by the same method as that used for a compact disk. The information on an analytical sample, analytical process, analytical result, etc. can be also stored by using a recordable compact disk or magnetic disk.

In The apparatus and method for detecting biomaterials has the following effects.

Firstly, since the present invention uses a disk-type substrate, a scanning device for analyzing the binding reaction of biomaterials such as a DNA chip, protein chip, peptide chip, etc. can be simplified, thus reducing the cost for detecting biomaterials.

Secondly, since the present invention stirs the sample solution by rotating the biochip, the reaction speed is increased, thus reducing the time for analysis.

Thirdly, since the present invention stores the information on biomaterial in the disk-type substrate, and records and detects contents, such as a sample, experimental procedure, result, etc., thus making it easier to manage analytical information.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A biochip, comprising:
   a substrate having a center hole at a central portion;
   a biomaterial region arrayed at a circumferential portion of the substrate; and
   an information region formed on the substrate between the biomaterial region and the center hole and having information on the biomaterials, wherein the information region has slits formed at a predetermined interval for providing information on positions, and has a reference slit for providing information on a reference position.

2. The biochip according to claim 1, wherein the substrate is made from any one of glass, silicon, acryl group, polycarbonate, PET (polyethylene terephtalate), polystyrene, or polypropylene.

3. The biochip according to claim 1, wherein the biomaterials of the biomaterial region are immobilized on the substrate by a covalent binding, and each different biomaterial is immobilized at a different position.

4. The biochip according to claim 1, wherein the biomaterial is one of DNA, RNA, PNA, oligonucleotides, peptides, protein, membrane, polysaccharides, antigen, antibody, or cells.

5. The biochip according to claim 1, wherein the biomaterials of the biomaterial region are arranged at the same interval in a radial direction of the substrate and at the same angle in a circumferential direction of the substrate.

6. The biochip according to claim 1, wherein the width of the reference slit is different from that of other slit.

7. The biochip according to claim 1, wherein the slits are formed of gold or aluminum.

8. In an apparatus for detecting biomaterials using a biochip including a substrate having a center hole at a central portion, a biomaterial region arranged at a circumferential portion of the substrate; and an information region formed on the substrate between the biomaterial region and the center hole, an apparatus for detecting biomaterials, comprising:
   a spindle motor mounted at the center hole of the biochip and adapted to rotate the biochip;
   a light source for irradiating light to the biochip;
   a mirror unit for selectively reflecting or transmitting the light emitted from the light source according to its wavelength;
   a head unit for receiving the light transmitted from the mirror unit and irradiating the same to the biomaterial region of the biochip;
   a detection unit for detecting the light emitted from the biomaterial region and analyzing the biomaterials; and
   an optical pickup unit for recording the information on the biomaterials on the information region of the biochip and reading out the information recorded on the information region.

9. The apparatus according to claim 8, wherein the head unit moves in a radial direction of the biochip.

10. The apparatus according to claim 8, wherein the mirror unit is a dichroic mirror.

11. The apparatus according to claim 8, wherein the detection unit is an APD (avalanche photodiode) or PMT (photomultiplier tube).

12. The apparatus according to claim 8, wherein the apparatus for detecting biomaterials further comprises an optical filter, lens, and pin hole between the mirror unit and the detection unit.

13. In a method for detecting biomaterials using the apparatus of claim 8, a method for detecting biomaterials, comprising the steps of:

mounting a biochip to the spindle motor; putting a sample solution into the biomaterial region of the biochip and rotating the biochip;

emitting the light from the first light source to thus be incident upon the biomaterial of the biochip;

making the light emitted from the biomaterial incident upon the detection unit and analyzing the biomaterials; and recording the information for analytes on the information region of the biochip and reading the same by means of the pickup unit.

14. The method according to claim 13, wherein the step of rotating the biochip includes the steps of:

placing the upper substrate on the biochip;

putting sample solution between the upper substrate and the biochip; and helping to diffuse the sample solution by rotating the biochip.

* * * * *